United States Patent [19]

Atsumi et al.

[11] Patent Number: 5,061,702
[45] Date of Patent: Oct. 29, 1991

[54] CEPHEM COMPOUND AS AN ANTIMICROBIAL AGENT

[75] Inventors: Kunio Atsumi; Katsuyoshi Iwamatsu; Kenji Sakagami; Takashi Yoshida; Haruo Yamamoto; Seiji Shibahara; Shigeharu Inouye, all of Yokohama, Japan

[73] Assignee: Meiji Seika Kabushiki Kaisha, Tokyo, Japan

[21] Appl. No.: 402,814

[22] Filed: Sep. 5, 1989

[30] Foreign Application Priority Data

Sep. 2, 1988 [JP] Japan .................................. 63-220198

[51] Int. Cl.$^5$ .................. C07D 501/24; A61K 31/545
[52] U.S. Cl. ...................................... 514/202; 540/222
[58] Field of Search ................. 540/222; 514/202, 229

[56] References Cited

U.S. PATENT DOCUMENTS 4,839,350 6/1989 Atsumi et al. ....................... 514/202

Primary Examiner—Nicholas S. Rizzo
Attorney, Agent, or Firm—Wenderoth, Lind & Ponack

[57] ABSTRACT

A novel cephem compound which has antimicrobial activity is disclosed. The cephem compound is represented by the formula:

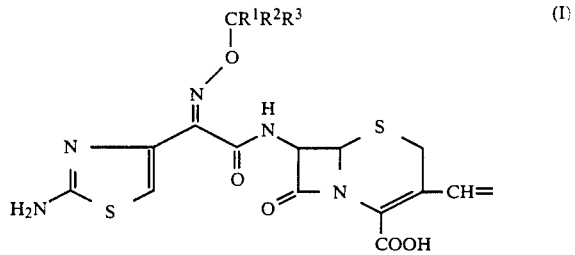

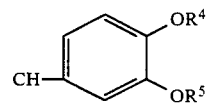

wherein $R^1$ represents a hydrogen atom or a carboxyl group; $R^2$ and $R^3$, which may be the same or different, each represent a hydrogen atom or a lower alkyl group of 1-3 carbon atoms; and $R^4$ and $R^5$, which may be the same or different, each represent a hydrogen atom or an acyl group; and pharmaceutically acceptable salts thereof.

4 Claims, No Drawings

CEPHEM COMPOUND AS AN ANTIMICROBIAL AGENT

BACKGROUND OF THE INVENTION

1. Field of the Art

This invention relates to a novel β-lactam antimicrobial agent and pharmaceutically acceptable salts thereof. In more detailed description, this invention relates to novel cephem compounds, pharmaceutically acceptable salts thereof and the process for preparing them, and relates further to an antimicrobial agent comprising the compound as an effective component. The compounds are useful as medical agents and animal drugs since they have an excellent effect on the therapy for diseases of human and other animals caused by pathogenic bacteria.

2. Related art

Cephem compounds which are structurally relative to the compounds of the present invention, for example, have been disclosed in Japanese patent Laid-Open Publication Nos. 124790/1980, 122388/1981 and 76083/1984. In addition, we have already discovered cephem compounds which are structurally relative to the compounds of the present invention and disclosed in Japanese patent Laid-Open Publication Nos. 178991/1986, 19593/1987 and 205088/1987 (These compounds have also the same substituted vinyl side chain as those of the compounds of this present invention (described in detail later) However, the compounds of the present invention are novel cephem compounds having a different substituent at the side chain from those of these known relative compounds)

Since cephalosporin antibiotics have a wide antimicrobial activity for Gram-positive and negative bacteria, various semi-synthesized cephalosporin compounds have already been prepared commercially and used clinically as therapeutic medicines for various infectious diseases. However, only a few among these medicines have an antimicrobial activity for *Pseudomonas aeruginosa* and Myxomycetes, and many of these medicines are unstable for β-lactamase produced by the resistant strain. Thus, these medicines have a defect that they have a low antimicrobial activity for the resistant strain, proposing a clinical problem (W. E. Wick., Chapter 11 in "Cephalosporins and Penicillins, Chemistry and Biology", edited by E. H. Flynn, Academic Press, New York, N.Y., 1972, ).

SUMMARY OF THE INVENTION

We have already disclosed a novel cephem compound having, at 3-position of the cephem ring, a vinyl group substituted with a hetero-ring at its β-position in Japanese patent Laid-Open Publication Nos. 178991/1986, 19593/1987 and 205088/1987 (described above). Now, in further studies, we have discovered that the novel cephem compounds shown in the formula (I) which is given hereinbelow have a wide and potent antimicrobial activity for Gram-positive and negative bacteria and particularly for *Pseudomonas aeruginosa*, and that the novel compound have a strong antimicrobial activity for various β-lactamase-producing bacteria and yet a low toxicity, and are well-absorbed.

Accordingly, this invention in one aspect provides a cephem compound represented by the general formula (I).

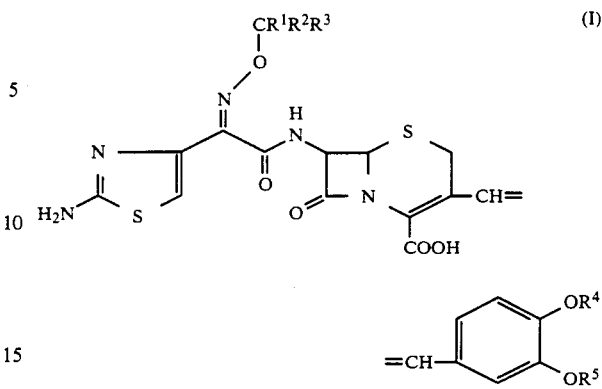

wherein $R^1$ represents a hydrogen atom or a carboxyl group; $R^2$ and $R^3$, which may be the same or different, each represent a hydrogen atom or a lower alkyl group of 1-3 carbon atoms; and $R^4$ and $R^5$, which may be the same or different, each represent a hydrogen atom or an acyl group.

Pharmaceutically acceptable salts of the cephem compound of the general formula is also provided.

This invention, in another aspect, provides an antimicrobial agent which comprises a cephem compound represented by the general formula (I) or a pharmaceutically acceptable salt thereof as an effective component.

Furthermore, this invention also relates to a process for preparing a cephem compound represented by the general formula (I) which comprises reacting a compound represented by the following general formula (II),

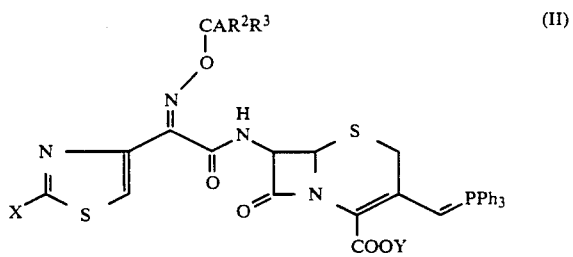

wherein A represents a hydrogen atom or a carboxyl group which may or may not be protected; $R^2$ and $R^3$, which may be the same or different, each represent a hydrogen atom or a lower alkyl group of 1-3 carbon atoms; X represents an amino group which may or may not be protected; Y represents a protecting group of the carboxyl group; and Ph represents a phenyl group, with a compound represented by the following general formula (III),

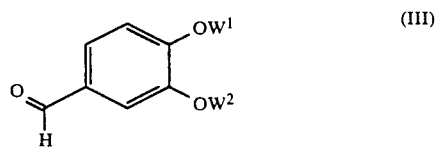

wherein $W^1$ and $W^2$, which may be the same or different, each represent a protecting group or an acyl group of the phenolic hydroxyl group, and removing the protecting group present from the reaction product, if necessary.

In addition, this invention provides another process for preparing a novel cephem compound represented by the general formula (I) which comprises reacting a compound represented by the general formula (IV),

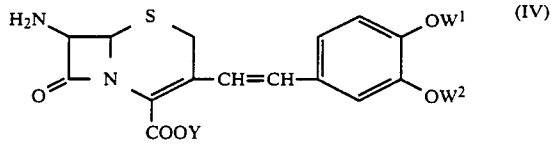

wherein Y represents a hydrogen atom or a protecting group of the carboxyl group; and $W^1$ and $W^2$, which may be the same or different, each represent a protecting group of the phenolic hydroxyl group or an acyl group, or its reactive derivative at the amino group or a salt thereof, with a compound represented by the general formula (V),

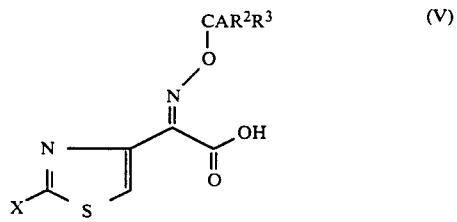

wherein A represents a hydrogen atom or a carboxyl group which may or may not be protected; $R^2$ and $R^3$, which may be the same or different, each represent a hydrogen atom or a lower alkyl group of 1-3 carbon atoms; and X represents an amino group which may or may not be protected, or its reactive derivative at the carboxyl group or a salt thereof, and removing the protecting group present from the reaction product, if necessary.

The novel cephem compounds of this invention have a wide and potent antimicrobial activity, and yet these compounds have a low toxicity and are well-absorbed. Thus, this invention presents excellent antimicrobial agents.

DETAILED DESCRIPTION OF THE INVENTION

Compounds

The compounds according to this invention are shown by the general formula (I).

The compounds of the general formula (I) include cis and trans isomers, depending on the position of the substituent of the vinyl side chain at the 3-position of the cephem ring. Thus, this invention includes cis and trans isomers, and mixtures thereof. Furthermore, the stereochemistry of the oxime of the side chain at the 7position shows that it is a syn-isomer.

In the compound shown in the general formula (I), the substituent $R^1$ represents a hydrogen atom or a carboxyl group, and preferably a carboxyl group.

The substituents $R^2$ and $R^3$ in the general formula (I) can be either the same or the different group and represent a hydrogen atom or a lower alkyl group of 1-3 carbon atoms such as methyl, ethyl, propyl or isopropyl, and preferably a hydrogen atom, methyl or ethyl group.

An acyl group which is one embodiment of the substituents $R^4$ and $R^5$ in the formula (I) is, for example, a lower alkanoyl group of preferably 1-4 carbon atoms such as formyl, acetyl, n-propanoyl, i-propanoyl, n-butanoyl or pivaloyl group, and the like, and an aroyl group including alkaroyl group, of preferably 6-10 carbon atoms such as benzoyl or toluoyl group and the like. It is to be understood that $R^4$ and $R^5$ are not limited to these groups described above. Preferably, $R^4$ and/or $R^5$ represent a hydrogen atom, acetyl, propanoyl or formyl group.

Examples of the compounds represented by the formula (I) in accordance with the present invention (including cis and trans isomers and their mixtures) are as follows, although it is to be understood that the present invention is not restricted thereto.

(a) (6R,7R)-7-[(Z)-2-(2-aminothiazol-4-yl)-2-methoxyiminoacetamido]-3-[2-(3,4-dihydroxyphenyl)vinyl]-ceph-3-em-4-carboxylic acid;

(b) (6R,7R)-7-[(Z)-2-(2-aminothiazol-4-yl)-2-methoxyiminoacetamido]-3-[2-(3,4-diacetoxyphenyl)vinyl]-ceph-3-em-4-carboxylic acid;

(c) (6R,7R)-7-[(Z)-2-(2-aminothiazol-4-yl)-2-(1-carboxy-1-methyl)ethoxyiminoacetamido]-3-[2-(3,4dihydroxyphenyl)vinyl]-ceph-3-em-4-carboxylic acid;

(d) (6R,7R)-7-[(Z)-2-(2-aminothiazol-4-Yl)-2-(1-carboxy-1-methyl)ethoxyiminoacetamido]-3-[2-(3,4-diacetoxyphenyl)vinyl]ceph-3-em-4-carboxylic acid; and (e) (6R,7R)-7-[(Z)-2-(2-aminothiazol-4-yl)-2-carboxymethoxyiminoacetamido]-3-[2-(3,4-diacetoxyphenyl)-vinyl]ceph-3-em-4-carboxylic acid.

The pharmaceutically acceptable salts of the compounds of this invention represented by the formula (I) include the medically acceptable salts, particularly conventional nontoxic salts; for example, alkali metal salts such as sodium salt and potassium salt and the like, alkaline earth metal salts such as calcium salt and magnesium salt and the like, and ammonium salt, and salts with an organic base; for example, salts with an organic amine such as triethylamine salt, pyridine salt, ethanolamine salt, triethanolamine salt and dicyclohexylamine salt and the like, and salts with a basic amino acid such as those with lysine and arginine.

Preparation of the compound (1)

The compounds of this invention represented by the formula (I) can be prepared by any suitable procedure including the introduction of substituent and/or the formation of linkage.

The preferred embodiments of the preparation procedures are shown below.

One of these procedures comprises reacting a compound of the formula (II),

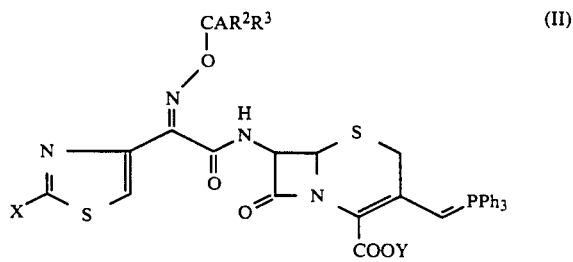

wherein A has the same meaning as $R^1$ or is a protected carboxyl group; $R^2$ and $R^3$ are defined hereinbefore; X represents an amino group or a protected amino group; and Y represents a protecting group of the carboxyl group, with a compound of the formula (III),

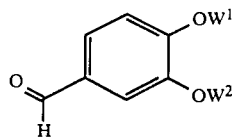
(III)

wherein $W^1$ and $W^2$ may be the same or different and each represent a protecting group of the phenolic hydroxyl group or an acyl group, and removing the protecting group present by a usual method, if necessary.

The protecting group of the amino group in the phosphorane (II) includes conventional protecting groups of an amino group which can be released easily by acid hydrolysis etc, such as an alkoxycarbonyl group such as tertiary butoxycarbonyl group; an acyl group such as formyl and chloroacetyl; and trityl group.

The protecting group Y of the carboxyl group includes conventional protecting groups which can be used in cephalosporins, such as for example, p-methoxybenzyl group, diphenylmethyl group, p-nitrobenzyl group, aryl group, a lower alkyl group, a lower alkoxymethyl group, a lower alkylthiomethyl group and a lower alkanoyloxymethyl group, and the like. Besides, the protecting group Y includes also metabolically unstable groups which can be hydrolyzed and removed in vivo, for example, a lower alkoxycarbonyloxyalkyl group and (2-oxo-1,3-dioxol-4-yl)methyl group which may or may not be protected.

The protecting group in the protected carboxyl group as one embodiment of A includes similar protecting groups to Y.

In the aldehyde (III), the protecting groups of the phenolic hydroxyl groups, $W^1$ and $W^2$, include protecting groups which can be conventionally applied to cephalosporins. For example, p-methoxybenzyl group, diphenylmethyl group, p-nitrobenzyl group, a lower alkoxymethyl group, a lower alkylthiomethyl group, and a lower alkanoyloxymethyl group, and further acyl groups such as acetyl group, pivaloyl group and benzoyl group, and the like can be also used as protecting groups of $W^1$ and $W^2$.

The phosphorane of the formula (II) can be prepared by the reaction of the formula (IV),

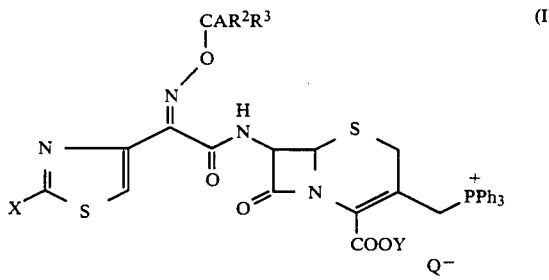
(IV)

wherein A, $R^2$, $R^3$, X and Y are defined hereinbefore, and Q represents a salt-forming anion, with an inorganic or organic base.

Examples of the salt-forming anions Q include inorganic anions such as chloride ion, bromide ion, iodide ion, ½ sulfate ion, hydrogensulfate ion, acetate ion or phosphate ion, and the like; and anions of organic sulfonates and carboxylates such as p-toluenesulfonate ion, methanesulfonate ion, oxalate ion, acetate ion, trifluoroacetate ion or formate ion, and the like.

Examples of inorganic or organic bases selected to react with the compound of the formula (IV) include: alkali metal hydroxide (for example, sodium hydroxide, potassium hydroxide etc.), alkaline earth metal hydroxide (for example, calcium hydroxide etc.), alkali metal bicarbonate (for example, sodium bicarbonate, potassium bicarbonate etc.), alkali metal carbonate (for example, sodium carbonate, potassium carbonate etc.), alkaline earth metal carbonate (for example, calcium carbonate etc.), tri(lower)alkylamine (for example, triethylamine, trimethylamine etc.), pyridine, N-(lower)alkylmorpholine, N,N-di(lower)alkylbenzylamine, and the like.

This reaction is generally carried out in a conventional solvent such as water, acetone, ethanol, propanol, methanol, dioxane, acetonitrile, chloroform, methylene chloride, tetrahydrofuran, ethyl acetate, N,N-dimethylformamide, and pyridine; and/or another organic solvent which does not give an adverse effect on the reaction. These solvents can be used in admixture with water or in a two-phase or layer with water. The reaction is usually carried out at any suitable temperature, and under cooling or heating. After the separation or without separation of the product, the phosphorane (II) produced by the reaction is subjected to the reaction with the aldehyde (III).

The reaction between the phosphorane (II) and the aldehyde (III) is usually carried out in a conventional solvent such as water, acetone, ethanol, propanol, methanol, dioxane, acetonitrile, chloroform, methylene chloride, tetrahydrofuran, ethyl acetate, N,N-dimethyl formamide, pyridine, and/or another organic solvent which does not give an adverse effect on the reaction. These solvents can be used in admixture with water or in two-phase or layer with water. Although the reaction temperature is not restricted to particularly levels, the reaction is usually carried out under cooling or heating.

The product thus obtained is the desired compound (I) of the present invention, which may be protected at the amino and carboxyl groups. Accordingly, if necessary, each protecting group can be removed by a conventional method. The method for the removal of the carboxyl and amino protecting groups is suitably selected, depending on the kind of the protecting group used. In order to release the amino protecting group, any conventional method such as hydrolysis or reduction etc can be applied. In the case where the protecting group is an acyl group, the reactions with imino halogenation agent and subsequent iminoetherification agent are applied, followed if necessary by hydrolysis. The method of hydrolysis with an acid is one of usual methods, and for example, it is applied to the removal of the group such as alkoxycarbonyl group, formyl group or trityl group. As the acid is suitably selected formic acid, trifluoroacetic acid or hydrochloric acid and the like, depending on the kind of the amino protecting group. The reaction can be performed in the absence of a solvent or in the presence of a solvent such as water, a hydrophilic organic solvent or a mixture thereof. When trifluoroacetic acid is used as an acid for hydrolysis, the reaction may be carried out in the presence of anisole. In order to release the carboxyl protecting group, any conventional method such as hydrolysis or reduction etc. can be applied. The hydrolysis with acid is one of usual methods, and, for example, it is applied to the removal of the group such as silyl group, p-methoxybenzyl group or diphenylmethyl group. In the case where the removal of the protecting group of the phenolic hydroxyl group is necessary, any conventional method such as hydrolysis or reduction etc. can be applied. Hydrolysis with an acid or a base is one of conventional methods for the removal of the protecting group of a phenolic hydroxyl group. For example, an acid is applied to the release of the groups such as p-methoxybenzyl group or diphenylmethyl group etc., and a base is applied to the release of the acyl group such as acetyl group or benzoyl group etc.

Preparation of the compound (2)

A further and preferred process for the preparation of the compound (I) is as follows.

The process comprises the reaction of a compound of the formula (IV),

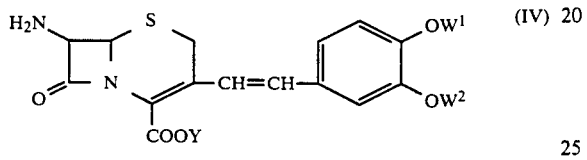

wherein $W^1$, $W^2$ and Z are defined hereinabove; and Y is defined hereinbefore or represents a hydrogen atom, or its reactive derivative at the amino group or a salt thereof, with a compound of the formula (V),

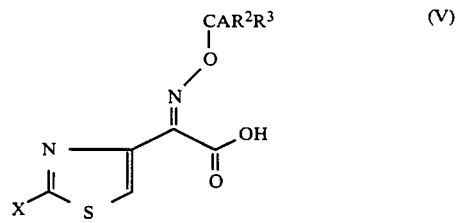

wherein A, $R^2$, $R^3$ and X are defined hereinabove, or its reactive derivative at the carboxyl group or a salt thereof.

Examples of the reactive derivatives at the amino group of the compound (IV) include: (a) an imino isomer or its tautomeric isomer of a Schiff base produced by the reaction between the compound (IV) and a carbonyl compound such as aldehyde or ketone etc.; (b) silyl derivatives produced by the reaction between the compound (IV) and bis(trimethylsilyl)acetamide etc.; (c) derivatives produced by the reaction between the compound (IV) and phosphorus trichloride or phosgene.

Examples of suitable salts of the compounds (IV) and (V) include: (a) acid-addition salts such as salts with organic acid, such as, for example, acetic acid, maleic acid, tartaric acid, benzenesulfonic acid, toluenesulfonic acid and the like, or salts with an inorganic acid such as, for example, hydrochloric acid, hydrobromic acid, sulfuric acid, phosphoric acid and the like; (b) metal salts such as alkali metal salts or alkaline earth metal salts, such as for example, sodium salt, potassium salt, calcium salt, magnesium salt and the like; (c) ammonium salts; and (d) salts with an organic amine, such as, for example, triethylamine salt, dicyclohexylamine salt, and the like.

Examples of the suitable reactive derivatives at the carboxyl group of the compound (V) include: acid halides, acid azide, acid anhydrides, activated amides or activated esters and the like, and more particularly (a) acid chlorides and acid bromides; (b) mixed acid anhydrides with an acid such as substituted phosphoric acid (for example, a dialkyl phosphate, dibenzyl phosphate, phosphorous halide etc.), a dialkyl phosphite, sulfurous acid, thiosulfuric acid, sulfuric acid, an alkyl carbonate (for example, methyl carbonate, ethyl carbonate etc.), an aliphatic carboxylic acid (for example, pivalic acid, valeric acid, isovaleric acid, butanoic acid, trichloroacetic acid etc.) or an aromatic carboxylic acid (for example, benzoic acid etc.); (c) activated amides with imidazole, dimethylpyrazole, triazole or tetrazole; (d) activated esters in a narrow sense, such as for example, a cyanomethyl ester, a methoxymethyl ester, a dimethyliminomethyl ester, a vinyl ester, a propargyl ester, a p-nitrophenyl ester, a 2,4-dinitrophenyl ester, a trichlorophenyl ester, a pentachlorophenyl ester, a mesylphenyl ester, a phenylazophenyl ester, a phenylthioester, a p-nitrophenylthioester, a p-cresylthioester, a carboxymethylthioester, a pyranyl ester, a pyridyl ester, a piperidyl ester, an 8-quinolyl thioester, and the like or activated esters in a wide sense such as ester with an N-hydroxy compound (for example, N,N-dimethylhydroxyamine, 1-hydroxy-2-(1H)-pyridone, N-hydroxysuccinimide, N-hydroxyphthalimide, 1-hydroxy-6-chloro-1H-benzotriazole etc.). These reactive derivatives are suitably selected, depending on the kind of the reactant compound (V).

The reaction between the compound (IV) and the compound (V) is usually carried out in a conventional solvent such as water, acetone, dioxane, acetonitrile, chloroform, methylene chloride, tetrahydrofuran, ethyl acetate, N,N-dimethylformamide, and pyridine; and/or another organic solvent which does not give an adverse effect on the reaction. These solvents can be used in admixture with water.

When the compound (V) is used as a free acid form or a salt form in the reaction, it is desirable to use a condensing agent. Examples of preferred condensing agents include: for example, N,N'-dicyclohexylcarbodiimide, N-cyclohexyl-N'-morpholinoethyl carbodiimide, N-cyclohexyl-N'-(4-diethylaminocyclohexyl) carbodiimide, N,N'-diethylcarbodiimide, N,N'-diisopropylcarbodiimide, N-ethyl-N'-(3-dimethylaminopropyl)carbodiimide, N,N-carbonylbis(2-methylimidazole), pentamethyleneketene-N-cyclohexylimine, diphenylketene-N-cyclohexylimine, ethoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide inner salt, 1-( p-chlorobenzenesulfonyloxy)-6-chloro-1H-benzotriazole, or so-called Vilsmeier's reagent produced by the reaction between dimethylformamide and thionyl chloride, phosgene or phosphorus oxychloride.

The reaction also can be carried out in the presence of inorganic base or organic base. Examples of these bases include: alkali metal bicarbonates (for example, sodium bicarbonate, potassium bicarbonate etc.), alkaline earth metal carbonates (for example, calcium carbonate etc.), tri(lower)alkylamines (for example, triethylamine, trimethylamine etc.), pyridine, N-(lower) alkylmorpholines, N,N-di(lower)alkylbenzylamines, and the like.

The reaction temperature is not restricted to particular levels, but the reaction is usually carried out under cooling or heating.

The product obtained by the second procedure (2) is the desired compound (I) of the present invention or the desired compound (I) protected at the amino and carboxyl groups. Accordingly, if necessary, each protecting group can be removed by a conventional method. The method for the removal of the carboxyl and amino protecting groups is suitably selected, depending on the kind of the protecting group which is removed. In order to remove an amino protecting group, any conventional method such as hydrolysis or reduction etc. can be applied. When the protecting group is an acyl group, the reactions with iminohalogenation agent and then with iminoetherification agent are applied, followed by hydrolysis, if necessary. The method of hydrolysis with acid is one of conventional methods, and, for example, it is applied to the removal of a group such as alkoxycarbonyl group, formyl group or trityl group. Also, any suitable acid such as formic acid, trifluoroacetic acid or hydrochloric acid etc. is selected depending on the kind of the amino protecting group. The reaction can be performed in the presence or absence of a solvent such as water, a hydrophilic organic solvent or a mixture thereof. When trifluoroacetic acid is used as an acid for hydrolysis, the reaction can be carried out in the presence of anisole. In order to remove the carboxyl protecting group, any conventional method such as hydrolysis or reduction etc. can be applied. Hydrolysis by an acid is one of usual methods, and for example, it is applied to the removal of the group such as silyl group, p-methoxybenzyl group or diphenylmethyl group. When removal of the protecting group of the phenolic hydroxyl group is necessary, any conventional method such as hydrolysis or reduction etc. can be applied. Hydrolysis by an acid or a base is one of usual methods for the removal of the protecting group of the phenolic hydroxyl group. For example, an acid is used to remove groups such as p-methoxybenzyl group or diphenylmethyl group etc., and a base is used to remove an acyl group such as acetyl group or benzoyl group etc.

The compound of the general formula (I) thus produced can be isolated from the reaction mixture by conventional methods.

For example, the isolation can be performed by a suitable combination of purification means such as purification by means of an adsorption resin such as, for example, "Amberlite XAD-2" (Rohm and Haas), "Diaion HP-20" or "Sephabeads SP 207" (Mitsubishi Kasei KK), a precipitation method and a crystallization method etc.

Use of the Compound/an Antimicrobial Agent

It is already described above that the compound shown in the general formula (I) or salts thereof have antimicrobial activity.

The antimicrobial agent comprising the compound (I) or salts thereof as a major component can be administered by either oral or parenteral route to human and other animals. Accordingly, the antimicrobial agent of this invention can be employed in the suitable formulation corresponding to the administration route. Particularly, it is used in various formulations as injection drugs for intravenous or intramuscular administration: oral drugs such as capsule, tablet or powder medicine; rectal administration drugs; such as fatty suppositories, water-soluble suppositories. These various formulations can be prepared by conventional methods using excipients, extending agents, binding agent, wetting agents, disintegrants, surfactants or wetting agents, lubricants, dispersing agents, buffers, preservatives, solubilizers, antiseptics, flavor or analgesia agents, and the like.

The dosage is suitably determined in consideration of age and symptom or condition of patients corresponding to each case, but a proposed dose of the compounds of the invention for administration to adult man is usually 250–3000 mg a day, which could be administered, for example, 1–4 times a day.

EXPERIMENTAL EXAMPLES

The present invention is precisely explained by the further examples below, but these examples should not be construed as limiting the invention.

(1) Synthesis of the compound

EXAMPLE 1

(6R,7R)-7-[(Z)-2-(2-aminothiazol-4-yl)-2-methoxyiminoacetamido]-3-[2-(3,4-diacetoxyphenyl)vinyl]ceph-3-em-4-carboxylic acid (a) To a solution (10 ml) in dichloromethane of 1.589 g of (6R,7R)-7-[(Z)-2-(2-tritylaminothiazol-4-yl) 2-methoxyiminoacetamido]-3-chloromethylceph-3-em-4-carboxylic acid p-methoxybenzyl ester, 0.551 g of triphenylphosphine, 0.315 g of sodium iodide and 10 ml of water were added at room temperature and the mixture was stirred for 6 hours. To the reaction mixture, 2.222 g of 3,4-diacetoxybenzaldehyde and 0.588 g of sodium bicarbonate were added and stirred for 14 hours at room temperature. The resulting dichloromethane layer was separated, concentrated under a reduced pressure, and was then purified by flash column chromatography (eluent, benzene:ethyl acetate=10:1) using Wako Gel C-300 (150 g, Wako Junyaku KK, Japan). The product, (6R,7R)-7-[(Z)-(2-tritylaminothiazol-4-yl)-2-methoxyiminoacetamido]-3-[2-(2,3-diacetoxyphenyl)vinyl]-ceph-3-em-4-carboxylic acid p-methoxybenzyl ester (0.904 g, a mixture of cis and trans isomers) was obtained.

(b) 0.870 g of (6R,7R)-7-[(Z)-2-(2-tritylaminothiazol-4-yl)-2-methoxyiminoacetamido]-3-[2-(3,4-diacetoxyphenyl)vinyl]ceph-3-em-4-carboxylic acid p-methoxybenzyl ester (a mixture of cis and trans isomers) obtained by the procedure (a) was dissolved in 1.8 g of anisole, and 9.0 ml of trifluoroacetic acid was added dropwise to the solution under ice cooling. After stirring for 1 hour at the temperature, 80 ml of i-propyl ether in an ice bath was added, and the resulting precipitate was filtered and dried under a reduced pressure. The precipitate dried was suspended in 5 ml of water and adjusted to pH 7.5 with 7% sodium bicarbonate solution under ice cooling to form a solution. Then the solution was purified by column chromatography using Diaion HP 20 resin (30 ml) (eluent, water, 30% aqueous acetone). The title compound (cis isomer: trans isomer =2:1) was obtained as sodium salt (0.291 g).

cis isomer

NMR ($D_2O$)$\delta$: 2.36(3H,s), 2.44 (3H, s), 3.27 (1H, d, J=18 Hz), 3.53(1H, d, J =18 Hz), 4.09 (3H, s), 5.36 (1H, d, J=5 Hz), 5.86(1H, d, J=5 Hz), 6.58 (1H, d, J=12 Hz), 6.72 (1H, d, J=12 Hz), 7.10 (1H, s), 7.1–7.5(3H, m).

trans isomer:

NMR (D₂O)δ: 2.44 (6H, s), 3.88(2H, broad s), 4.09 (3H, s), 5.36(1H, d, J =5 Hz), 6.86(1H, d, J=16 Hz), 6.74(1H, s), 7.1-7.5(4H, m).

EXAMPLE 2

(6R,7R)-7-[(Z)-2-(2-aminothiazol-4-yl)-2-methoxyiminoacetamido]-3-[2-(3,4-dihydroxyphenyl)vinyl]-ceph-3-em-4-carboxylic acid 0.230 g of (6R, 7R)-7[(Z)-2-(2-aminothiazol-4-yl)-2-methoxyiminoacetamido]-3-[2-(3,4-diacetoxyphenyl) vinyl]ceph-3-em-4-carboxylic acid sodium salt (a mixture of cis isomer: trans isomer=2:1) obtained in Example 1 was dissolved in 3 ml of 5% sodium bicarbonate aqueous solution and stirred for 2.5 hours at room temperature. The reaction mixture was purified by column chromatography using Diaion HP 20 resin (30 ml) (eluent, water, 30% aqueous methanol), and the title compound (a mixture of cis isomer : trans isomer =1:1) was obtained as sodium salt (0.165 g).

NMR(D₂O)δ: 3.32(0.5H, d, J=18 Hz), 3.48(0.5H, d, J=18 Hz), 3.77(1H, broad s), 4.08(1.5H), s), 4.10(1.5H, s), 5.30(0.5H, d, J=5 Hz), 5.35(0.5H, d, J=5 Hz), 5.90(0.5H, d, J=5 Hz), 6.39(0.5 Hz, d, J=12 Hz), 6.59(0.5 Hz, d, J=12 Hz), 6.72(0.5H, d, J=16 Hz) 6.8-7.1(4H, m), 7.20(0.5H, d, J=16 Hz).

EXAMPLE 3

(6R,7R)-7-[(Z)-2-(2-aminothiazol-4-yl)-2-(1-carboxy-1-methyl)ethoxviminoacetamido]-3-[2-(3,4-diacetoxyphenyl)vinyl]ceph-3-em-4-carboxylic acid (a) To a solution (6 ml) in dichloromethane of 0.923 g of (6R, 7R)-7-[(Z)-2-(2-aminothiazol-4-yl)-2-(1-t-butoxycarbonylethoxy-1-methyl)iminoacetamido]-3-chloromethylceph-3-em-4-carboxylic acid p-methoxybenzyl ester, 0.275 g of triphenylphosphine, 0.157 g of sodium iodide and 6 ml of water were added at room temperature and the mixture was stirred for 6 hours. To the reaction mixture, 0.666 g of 3,4-diacetoxybenzaldehyde and 0.294 g of sodium bicarbonate were added and the mixture was stirred for 14 hours at room temperature. The resulting dichloromethane layer was separated, concentrated under a reduced pressure, and was then purified by flash column chromatography using Wako Gel C-300 (70 g, Wako Junyaku KK, Japan) (eluent, benzene: ethyl acetate =10:1). The product, (6R,7R)-7-[(Z)-2-tritylaminothiazol-4-yl)-2-(1-methyl-1-t-butoxycarbonyl)ethoxyiminoacetamido]-3-[2-(3,4-diacetoxyphenyl)vinyl]ceph-3-em-4-carboxylic acid p-methoxybenzyl ester (0.447 g, a mixture of cis and trans isomers) was obtained.

(b) 0.432 g of (6R,7R)-7-[(Z)-2-(2-tritylaminothiazol-4-yl)-2-(1-t-butoxycarbonyl-1-methylethoxy)iminoacetamido]-3-[2-(3,4-diacetoxyphenyl) vinyl]-ceph-3-em-4-carboxylic acid p-methoxybenzyl ester (a mixture of cis and trans isomers) obtained by the procedure (a) was dissolved in 0.9 g of anisole, and 5.0 ml of trifluoroacetic acid was added dropwise to the solution under ice cooling. After stirring for 3.5 hours at the temperature, 50 ml of i-propyl ether in an ice bath was added, and the resulting precipitate was filtered and dried under a reduced pressure. The precipitate dried was suspended in 3 ml of water and adjusted to pH 7.5 with 7% sodium bicarbonate solution under ice cooling to form a solution. Then the solution was purified by column chromatography using Diaion HP 20 resin (30 ml) (eluent, water, 20% aqueous methanol). The title compound (cis isomer:trans isomer=1:1) was obtained as sodium salt (0.105 g).

NMR(D₂O)δ: 1.60(1.5H, s), 1.65(3H, s), 1.67(1.5H, s) 2,40 (1.5H, s), 2.48 (3H, s) 2.49 (1.5H, s), 3,31(0.5H, d, J=18 Hz), 3,54 (0.5H, d, J =18 Hz), 3,88(0.5H, d, J=18 Hz), 3.95(0.5H, d, J=18 Hz), 5.38(0.5H, d, J=5 Hz), 5.41 (0.5H, d, J=5 Hz), 5.88(0.5H, d, J=5 Hz), 5.97(0.5H, d, J=5 Hz), 6.60(0.5H), d, J=12Hz), 6.73 (0.5H, d, J=12 Hz) 6.92(0.5H, d, J=16 Hz), 7.10(0.5H, s), 7.12(0.5H, s), 7.2-7.65(3.5H, m).

EXAMPLE 4

(6R,7R)-7-[(Z)-2-(2-aminothiazol-4-y1)-2-(1-carboxy-1-methyl)ethoxyiminoacetamido]-3-[2-(3,4-dihydroxyphenyl) vinyl]ceph-3-em-4-carboxylic acid 0.070 g of (6R,7R)-7-[(Z)-2-(2-aminothiazol-4-yl)-2-(1-carboxy-1-methyl)ethoxyiminoacetamido]-3-[2-(3,4-diacetoxyphenyl)vinyl]ceph-3-em-4-carboxylic acid sodium salt (a mixture of cis isomer:trans isomer=1:1) obtained in Example 3 was dissolved in 3 ml of 5% sodium bicarbonate aqueous solution and stirred for 2.5 hours at room temperature. The reaction mixture was purified by column chromatography using Diaion HP 20 resin (20 ml) (eluent, water, 20% aqueous methanol), and the title compound (a mixture of cis isomer : trans isomer =1:2) was obtained as sodium salt (0.050 g).

cis isomer

NMR(D₂O)δ: 1.64(6H, s), 3.36(1H, d, J=18 Hz), 3.53(1H, d, J=18 Hz), 5.38 (1H, d, J=5 Hz), 5.8(1H, d, J=5 Hz), 6.43(1H, d, J=12 Hz), 6.62(1H, d, J=12 Hz), 6.9-7.4 (3H, m).

trans isomer;

NMR(D₂O)δ: 1.64(6H, s), 3.79(1H, d, J=18 Hz) 3.92(1H, d, J=18 Hz), 5.36(1H, d, J=5Hz), 5.92(1H, d, J=5 Hz), 6.80(1H, d, J=16 Hz), 6.9-7.4(4H, m).

EXAMPLE 5

(6R,7R)-7-[(Z)-2-(2-aminothiazol-4-yl)-2-carboxymethoxyiminoacetamido]-3-[2-(3,4-diacetoxyphenyl)-vinyl]ceph-3-em-4-carboxylic acid (a) To a solution (20 ml) in acetone of 2.6004 g of (6R, 7R)-7-phenylacetamido-3-chloromethylceph-3-em-4-carboxylic acid p-methoxybenzyl ester were dissolved 0.787 g of sodium iodide and 1.377 g of triphenylphosphine and the mixture was stirred for 1 hour. The reaction mixture was concentrated under a reduced pressure, and 25 ml of methylene chloride and 25 ml of water were added to the residue to form two layers. To the reaction mixture, 5.555 g of 2,3-diacetoxybenzaldehyde and 1.47 g of sodium bicarbonate were added and the mixture was stirred for 14 hours at room temperature. The resulting dichloromethane layer was separated, concentrated under a reduced pressure, and was then purified by flash column chromatography using Wako Gel C-300 (300 g, Wako Junyaku KK) (eluent, benzene:ethyl acetate=5:1). The product, (6R,7R)-7-phenylacetamido-3-[2-(3,4-diacetoxyphenyl)vinyl]-ceph-3-em-4-carboxylic acid p-methoxybenzyl ester (1.570 g, cis isomer) was obtained.

NMR(CDCl₃)δ:2.23(3H, s), 2.28(3H, s), 3.16(2H, broad s), 3.60(2H, s), 3.76(3H, s), 4.96(1H, d, J=5Hz), 5.66(1H, dd, J=5 Hz, 8 Hz), 6.39(1H, d, J=8 Hz), 6.51(1H, d, J=12Hz), 6.63(1H, d, J =12 Hz), 6.85-6.9(2H, m), 6.9-7.5(10H, m).

(b) To a solution (20 ml) in methylene chloride of 1.52 g of (6R,7R)-7-phenylacetamido-3-[2-(3,4-diacetoxyphenyl)vinyl]ceph-3-em-4-carboxylic acid p-methoxybenzyl ester (cis isomer) obtained by the procedure (a), 0.49 g of pyridine and 0.862 g of phosphorus pentachloride were added to the solution at $-20°$ C. After stirring for 2 hours under ice cooling, the reaction mixture was added to 30 ml of methanol cooled at $-40°$ C with shaking. After standing for 14 hours at 4° C., the solution was added to the mixture of 50 ml of water and 30 ml of methylene chloride under ice cooling. The reaction mixture was adjusted to pH 3.4 with sodium bicarbonate under ice cooling. The resulting organic layer was separated, and the water layer was subjected to extraction with 30 ml of methylene chloride, and the extract was combined with the organic layer. The combined solution was washed with 30 ml of 5% sodium bicarbonate and subsequently with 30 ml of saturated aqueous sodium chloride. The solution was dried with magnesium sulfate, concentrated under a reduced pressure and purified by flash column chromatography using Wako Gel C-300 (70 g, Wako Junyaku KK) (eluent, benzene ethyl acetate=1:1). The product, (6R, 7R)-7-amino-3-[2-(3,4-diacetoxyphenyl)vinyl]ceph-3-em-4-carboxylic acid p-methoxybenzyl ester (0.456 g, cis isomer) was obtained.

$NMR(CDCl_3)\delta$:1.6(2H, broad), 2.26(6H, s), 3.23(1H, d, J =18Hz), 3.35(1H, d, J=18 Hz), 3.77(3H, s), 4.69(1H, d, J =5 Hz), 4.93(1H, d, J=5Hz), 5.17(2H, s), 6.50(2H, s), 6.75–6.9(2H, m), 7.0–7.1(2H, m), 7.1–7.4(3H, m).

(c) To a suspension in 10 ml of methylene chloride of 0.371 g of (Z)-(2-tritylaminothiazol-4-yl)-2-(t-butoxycarbonylmethoxyimino)acetic acid and 0.109 g of 1-hydroxybenzotriazole monohydrate, 0.147 g of dicyclohexylcarbodiimide was added under ice cooling, and the mixture was stirred for 1 hour. To the reaction solution, 0.335 g of (6R,7R)-7-amino-3-[2-(3,4-diacetoxyphenyl)vinyl]ceph-3-em-4-carboxylic acid p-methoxybenzyl ester (cis isomer) obtained by the procedure (b) was added and the mixture was stirred for 15 hours at the temperature. After filtration of the insoluble matters, the solution was concentrated under a reduced pressure, and was then purified by flash column chromatography using Wako Gel C-300 (70 g, Wako Junyaku KK) (eluent, benzene:ethyl acetate=1:1). The produce, (6R, 7R)-7-[(Z)-2-(2-tritylaminothiazol-4-yl)-2-(t-butoxycarbonylmethoxyimino)acetamido]-3-[2-(3,4-diacetoxyphenyl)vinyl]ceph-3-em-4-carboxylic acid p-methoxybenzyl ester (0.448 g, cis isomer) was obtained.

$NMR(CDCl_3)\delta$:1.41(9H, s), 2.22(3H, s), 2.26(3H, s), 3.19(1H, d, J=18 Hz), 3.33 (1H, d, J=18 Hz), 3.77(3H, s) 4.71(2H, broad s), 5.04(1H, d, J=5 Hz), 5.15(2H, s), 5.84(1H, dd, J=5 Hz, 8 Hz), 6.47(1H, d, J=12 Hz), 6.55 (1H, d, J=12 Hz), 6.75–7.5 (23H, m), 8.44(1H, d, J=8 Hz)

(d) 0.440 g of (6R,7R)-7-[(Z)-2-(2-tritylaminothiazol-4-yl)-2-(t-butoxycarbonylmethoxyimino) acetamido]-3-[2-(3,4-diacetoxyphenyl)vinyl]ceph-3-em-4-carboxylic acid p-methoxybenzyl ester (cis isomer) obtained by the procedure (c) was dissolved in 0.9 g of anisole, and 5.0 ml of trifluoroacetic acid was added dropwise to the solution under ice cooling. After stirring for 3.5 hours at the temperature, 50 ml of i-propyl ether in an ice bath was added, and the resulting precipitate was filtered and dried under a reduced pressure. The precipitate dried was suspended in 3 ml of water and adjusted to pH 7.5 with 7% sodium bicarbonate solution under ice cooling to form a solution. Then the solution was purified by column chromatography using Diaion HP 20 resin (30 ml) (eluent, water, 20% aqueous methanol). The title compound (cis isomer) was thus obtained as sodium salt (0.176 g).

$NMR(D_2O)\delta$:2.39(3H, s), 2.48(3H, s), 3.31(1H, d, J =18 Hz), 3.56(1H, d, J=18 Hz), 4.69(2H, s), 5.39(1H, d, J =5 Hz), 5.88(1H, d, J=5 Hz), 6.59(1H, d, J=12 Hz), 6.73 (1H, d, J=12 Hz), 7.16(1H, s) 7.25–7.55(3H, m).

(2) Preparation of an antimicrobial agent

EXAMPLE 6

Formulation for injection

The solution containing the compound of Example 5 was aseptically pipetted into each vial so that it contained 1000 mg (titer)/vial.

EXAMPLE 7

Capsule the compound of Example 5 250 parts (titer)
lactose 60 1 parts (titer)
magnesium stearate 5 parts (titer)

These compounds were mixed uniformly and filled into each capsule so that it contained 250 mg (titer)/capsule.

EXAMPLE 8

Soft capsule for rectal administration

To a basis consisting of:
olive oil 160 parts
polyoxyethylenelaurylether 10 parts
sodium hexametaphosphate 5 parts The compound of Example 5 (25 parts, titer) was added and uniformly mixed and filled into each soft capsule for rectal administration so that it contained 250 mg (titer)/capsule.

(3) Antimicrobial activity

The compound (I) of the present invention and salts thereof are novel compounds and show an antimicrobial activity high enough to inhibit the growth of a wide range of pathogenic bacteria, including Gram-positive and negative bacteria. For some % the compounds (I) of this invention, the antimicrobial activities measured by the agar dilution method are given in Table I in order to show the utility of the compound (I) of the invention. The agar dilution method was carried out according to the method reported in *Chemotherapy*, 1981, vol. 29, 76–79 pp.

TABLE I

| MINIMUM GROWTH INHIBITION CONCENTRATION (µg/ml) | | | | | | |
|---|---|---|---|---|---|---|
| | Example 1 | Example 2 | Example 3 | Example 4 | Example 5 | Ceftazidime |
| *Staphylococcus aureus* 209P JC-1 | 12.5 | 12.5 | 50 | 50 | 25 | 3.13 |
| *Bacillus subtilis* ATCC 6633 | 3.13 | 3.13 | 25 | 25 | 25 | 3.13 |
| *Escherichia coli* No. 29 | 0.20 | 0.20 | 0.20 | 0.39 | 0.20 | 0.20 |
| *Escherichia coli* No. 255 | 0.10 | 0.10 | 0.10 | 0.10 | 0.39 | 25 |

TABLE I-continued

| MINIMUM GROWTH INHIBITION CONCENTRATION (μg/ml) | | | | | |
|---|---|---|---|---|---|
| | Example 1 | Example 2 | Example 3 | Example 4 | Example 5 | Ceftazidime |
| *Klebsiella pneumoniae* GN69 | 0.20 | 0.20 | 0.20 | 0.20 | 0.20 | 0.10 |
| *Proteus vulgaris* GN76 | 0.20 | 0.20 | 0.05 | 0.10 | 0.05 | 0.05 |
| *Citrobacter freundii* GN346 | 12.5 | 12.5 | 6.25 | 12.5 | 1.56 | 25 |
| *Enterobacter cloacae* GN7471 | 3.13 | 1.56 | 3.13 | 6.25 | 1.56 | 3.13 |
| *Serratia marcescens* No. 1 | 0.39 | 0.39 | 0.20 | 0.39 | 0.20 | ≦0.025 |
| *Pseudomonas aeruginosa* M-0148 | 1.56 | 1.56 | 0.39 | 0.39 | 0.20 | 1.56 |
| *Pseudomonas aeruginosa* E-2 | 0.39 | 0.39 | 0.05 | 0.20 | 0.10 | 0.39 |
| *Pseudomonas aeruginosa* IAM-1007 | 0.78 | 0.78 | 0.20 | 0.39 | 0.20 | 0.78 |
| *Pseudomonas cepacia* M-0527 | ≦0.025 | ≦0.025 | ≦0.025 | ≦0.025 | ≦0.025 | 0.39 |

We claim:

1. A cephem compound represented by the formula (I):

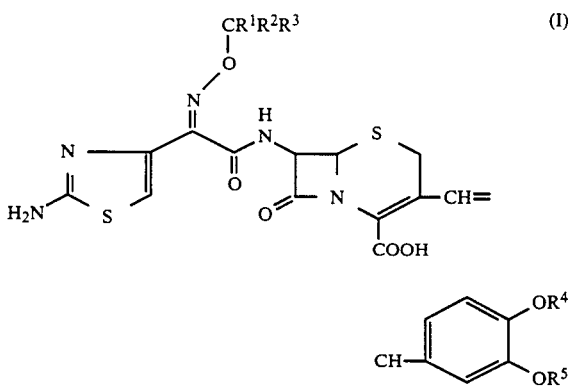

wherein $R^1$ represents a hydrogen atom or a carboxyl group; $R^2$ and $R^3$, which may be the same or different, each represent a hydrogen atom or a lower alkyl group of 1-3 carbon atoms; and $R^4$ and $R^5$, which may be the same or different, each represents a hydrogen atom or a lower alkanoyl group of 1-4 carbon atoms or an aroyl group of 6-10 carbon atoms; and pharmaceutically acceptable salts thereof.

2. The cephem compound as claimed in claim 1, which is selected from the group consisting of:
   (a) (6R,7R)-7-[(Z)-2-(2-aminothiazol-4-yl)-2-methoxyiminoacetamido]-3-[2-(3,4-dihydroxyphenyl)-vinyl]-ceph-3-em-4-carboxylic acid;
   (b) (6R,7R)-7-[(Z)-2-(2-aminothiazol-4-yl)-2-methoxyiminoacetamido]-3-[2-(3,4-diacetoxyphenyl)-vinyl]ceph-3-em-4-carboxylic acid;
   (c) (6R,7R)-7[(Z)-2-(2-aminothiazol-4-yl)-2-(1-carboxy-1-methyl)ethoxyiminoacetamido]-3-[2-(3,4-dihydroxyphenyl)vinyl]ceph-3-em-4-carboxylic acid;
   (d) (6R,7R)-7-[(Z)-2-(2-aminothiazol-4-yl)-2-(1-carboxy-1-methyl)ethoxyiminoacetamido]-3-[2-(3,4-diacetoxyphenyl)vinyl]ceph-3-em-4-carboxylic acid; and
   (e) (6R,7R)-7-[(Z)-2-(2-amiothiazol-4-yl)-2-carboxymethoxyiminoacetamido]-3-[2-(3,4-diacetoxyphenyl)vinyl]ceph-3-em-4-carboxylic acid.

3. The antimicrobial agent as claimed in claim 1, wherein the cephem compound is selected from the group consisting of:
   (a) (6R,7R)-7-[(Z)-2-(2-aminothiazol-4-yl)-2methoxyiminoacetamido]-3-[2-(3,4-dihydroxyphenyl)-vinyl]ceph-3-em-4-carboxylic acid;
   (b) (6R,7R)-7-[(Z)-2-(2-aminothiazol-4-yl)-2-methoxyiminoacetamido]-3-[2-(3,4-diacetoxyphenyl)-vinyl]ceph-3-em-4-carboxylic acid;
   (c) (6R,7R)-7-[(Z)-2-(2-aminothiazol-4-yl)-2-(1-carboxy-1-methyl)ethoxyiminoacetamido]-3-[2-(3,4-dihydroxyphenyl)vinyl]ceph-3-em-4-carboxylic acid;
   (d) (6R,7R)-7-[(Z)-2-(2-aminothiazol-4-yl)-2-(1-carboxy-1-methyl)ethoxyiminoacetamido]-3-[2-(3,4diacetoxyphenyl)vinyl]ceph-3-em-4-carboxylic acid; and
   (e) (6R,7R)-7-[(Z)-2-(2-aminothiazol-4-yl)-2carboxymethoxyiminoacetamido]-3-[2-(3,4-diacetoxyphenyl)vinyl]ceph 3-em-4-carboxylic acid.

4. An antimicrobial agent which comprises a cephem compound represented by the formula (I):

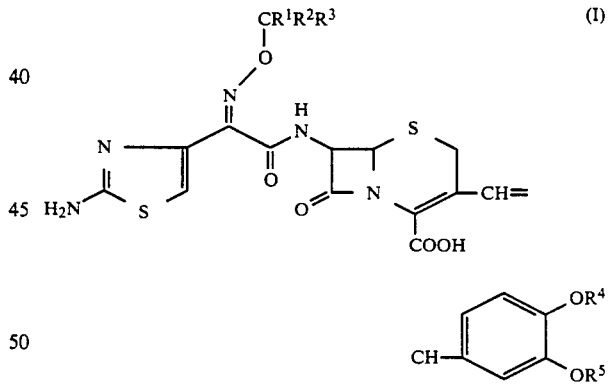

wherein $R^1$ represents a hydrogen atom or a carboxy group; $R^2$ and $R^3$, which may be the same or different, each represent a hydrogen atom or a lower alkyl group of 1-3 carbon atoms; and $R^4$ and $R^5$, which may be the same or different, each represent a hydrogen atom or a lower alkanoyl group of 1-4 carbon atoms or an aroyl group of 6-10 carbon atoms; and pharmaceutically acceptable salts thereof in conjunction with a pharmaceutically acceptable carrier therefor.

* * * * *